(12) United States Patent
Cerasoli et al.

(10) Patent No.: US 8,211,047 B2
(45) Date of Patent: Jul. 3, 2012

(54) BLOOD FILTERING DEVICE

(75) Inventors: Paolo Cerasoli, San Giovanni Teatino (IT); Fabio Arrizza, San Giovanni Teatino (IT)

(73) Assignee: Glomeria Therapeutics SRL, San Giovanni Teatino (IT)

( * ) Notice: Subject to any disclaimer, the term of this patent is extended or adjusted under 35 U.S.C. 154(b) by 541 days.

(21) Appl. No.: 11/920,551

(22) PCT Filed: May 18, 2006

(86) PCT No.: PCT/IB2006/051579
§ 371 (c)(1),
(2), (4) Date: Nov. 16, 2007

(87) PCT Pub. No.: WO2006/123308
PCT Pub. Date: Nov. 23, 2006

(65) Prior Publication Data
US 2009/0093747 A1    Apr. 9, 2009

(30) Foreign Application Priority Data
May 19, 2005    (IT) .............................. RM2005A0247

(51) Int. Cl.
*A61M 37/00*    (2006.01)
*C02F 1/44*    (2006.01)

(52) U.S. Cl. ............... 604/5.04; 604/4.01; 604/5.01; 604/6.09; 604/6.11; 210/645; 210/646; 210/739; 422/44

(58) Field of Classification Search ............ 604/4.01, 604/5.01, 5.04, 6.09, 6.11; 210/645, 646, 210/195.2
See application file for complete search history.

(56) References Cited

U.S. PATENT DOCUMENTS

| 4,083,777 | A | * | 4/1978 | Hutchisson | ............ 210/646 |
| 4,231,871 | A | | 11/1980 | Lipps et al. | |
| 4,269,708 | A | * | 5/1981 | Bonomini et al. | ........ 210/90 |
| 4,479,762 | A | * | 10/1984 | Bilstad et al. | ............ 417/395 |
| 4,765,437 | A | * | 8/1988 | Harwood et al. | ........ 181/282 |
| 5,232,437 | A | * | 8/1993 | Lysaght et al. | ......... 604/6.04 |
| 5,270,005 | A | | 12/1993 | Raible | |
| 5,895,571 | A | | 4/1999 | Utterberg | |
| 6,196,992 | B1 | * | 3/2001 | Keilman et al. | ........ 604/67 |

FOREIGN PATENT DOCUMENTS

| EP | 0 005 266 | 11/1979 |
| EP | 0 611 227 | 8/1994 |
| EP | 1 529 545 | 5/2005 |
| WO | 2004/069308 | 8/2004 |

OTHER PUBLICATIONS

International Search Report for PCT/IB2006/051579 mailed Nov. 30, 2006.

* cited by examiner

*Primary Examiner* — Leslie Deak
(74) *Attorney, Agent, or Firm* — Nixon & Vanderhye P.C.

(57) ABSTRACT

Blood filtering device (1), comprising: * a filter body (3; 103), having an inlet port (4; 104) for blood to be filtered; * a delivery flexible hose (5; 105) of the blood to be filtered, apt to be connected to said inlet port (4; 104) and to further ducts linked to a circulatory system; * peristaltic pump means (10; 105, 109, 114, 115, 117, 118, 143, 144, 145), wherein a case (16; 116) forms at least one peristaltic pump rotor chamber (13; 114), apt to house inside a portion of said delivery flexible hose (5; 105) for obtaining a peristaltic effect, wherein said case (16; 116) defines means for maintaining said filter body (3; 103) in a working position.

22 Claims, 4 Drawing Sheets

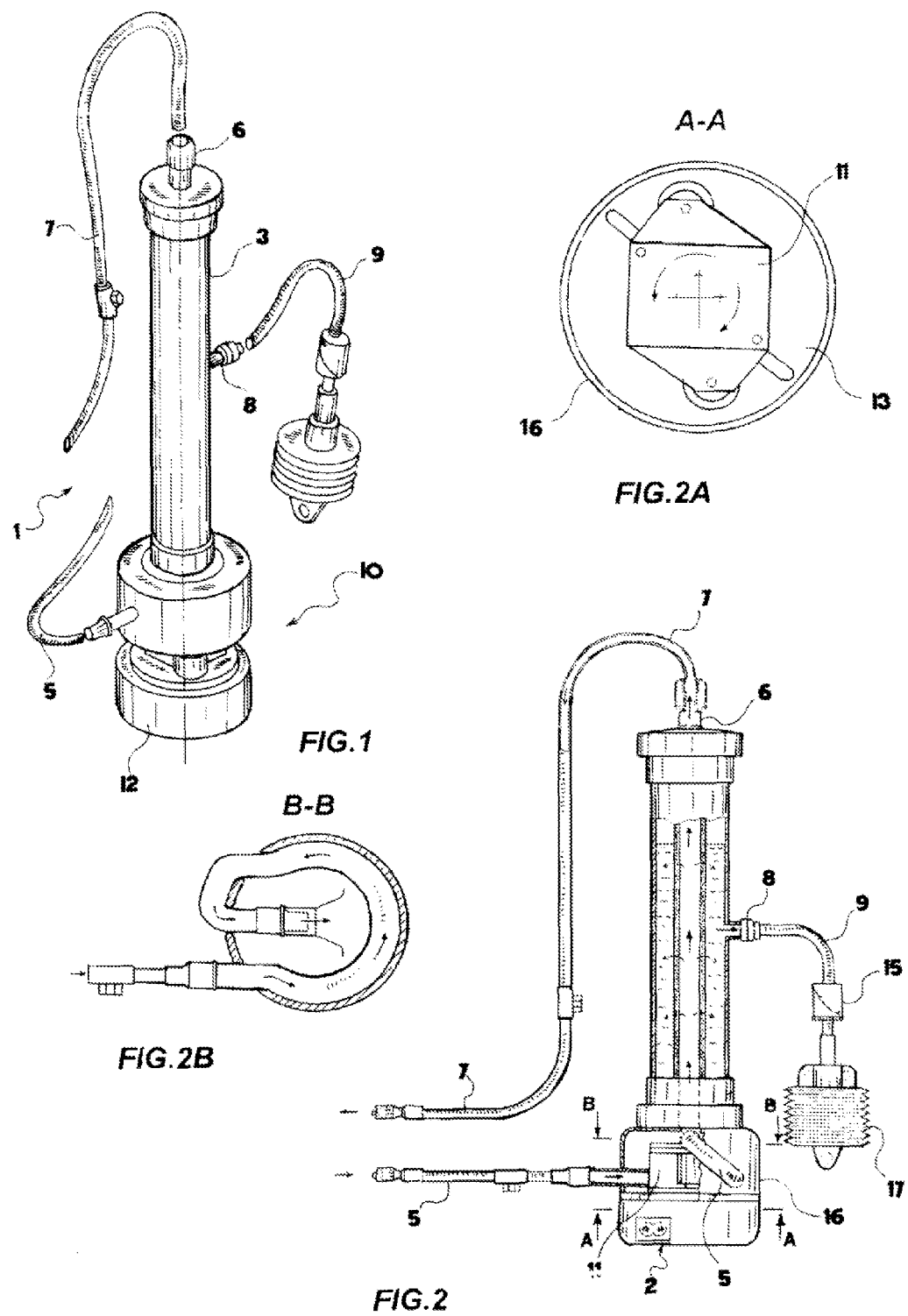

BLOOD FILTERING DEVICE

This application is the U.S. national phase of International Application No. PCT/IB2006/051579 filed 18 May 2006 which designated the U.S. and claims priority to Italian Patent Application No. RM2005A000247 filed 19 May 2005, the entire contents of each of which are hereby incorporated by reference.

The present invention relates to the field of blood filtration, in particular to devices for blood ultrafiltration in hyperhydrated patients and to methods for treating said patients.

BACKGROUND OF THE INVENTION

Isolated Ultrafiltration is often the only technique which allows saving human lives in the context of intensive therapy both for resuscitation and in cardiology. Although the technique is simple, it is carried out with complex dialysis equipments, which imply not only handling problems, but also evident problems for their high purchase, managing and maintenance costs.

In order to remove liquids from hyperhydrated patients in critical cardiovascular conditions, this technique is preferred to standard hemodialysis, thanks its characteristic feature of low flow both of blood feeding and ultrafiltration. The absence of dialysis bath and the relative circulation and control systems makes possible to design an equipment for Slow Continuous Ultrafiltration (S, C. U-F.) for a review of this technique, see Merril, RH/. "The technique of slow continuous ultrafiltration. Steps to maintain fluid balance without hemodynamic instability"; J. Crit. IHn.; 1991 March; 6(3).-289-94.

U.S. Pat. No. 6,514,226 teaches the treatment of patients affected by Congestive Heart Failure (CHF) by means of perfusion of a hemofilter through a suitable peristaltic pump. A depression is applied to the filter, which produces an ultrafiltration liquid; the amount of removed ultrafiltration liquid depends on the level of cardiocirculatory overload.

A more complex system is disclosed in U.S. Pat. No. 6,685,664, wherein a machine for extracorporeal treatment of blood substantially comprises withdrawal and return pipes, a pump for blood transfer, a hemofilter and control devices. The pump and the hemofilter are separated and mounted on a device controlling system operation. This machine is then mounted on a wheeled trestle. The whole system can be easily moved near the patient, however the overall size is considerable and it is unsuitable for use outside a hospital. A similar system is shown in US 2004054315.

A general common knowledge of this field and, in particular, the above mentioned patent and non-patent references are referred to for a complete picture of the state of the art.

There is still the need to have available a portable device for blood ultrafiltration, which maintains the efficacy of the known devices and of dialysis machines and allows its use outside the hospital premises, for example at patient's home, in the ambulance, in emergency situations, for example in field hospitals, in natural disaster situations, rescue in wilderness or places difficult to reach. Another need is to minimize the length of connecting tubes between patient and device, so as to use less blood possible to prime the pump-filter system, and anyway reduce blood residence time outside blood circle.

The present invention is focused to solve the above mentioned problems by providing a device essentially formed by a hemofilter incorporated with the pumping system.

SUMMARY OF THE INVENTION

The present invention provides an extremely simplified construction of a device for blood filtration, in particular ultrafiltration, which solves the disadvantages of the state of the art, especially with respect to complexity of traditional hemodialysis machines, portability, readiness of use, cost and training of people dedicated to patient's treatment.

The device of the present invention, as defined in appended claim 1, comprises a hemodialysis filter, in which a pump has been incorporated, which is suited to filter feeding directly from patient, thus substantially reducing blood withdrawal and return catheter tubing length.

It is to be underlined that it is very important to reduce catheter tubing length, not only from the point of view of working of the device, namely reducing the complexity of its components and its maintenance, but also from the point of view of the patient undergoing ultrafiltration. In fact, the possibility to shorten tubing makes the device more easy to handle, for example it can be placed directly side by side the patient, but requires much less blood to prime the pump that assures blood transfer through the filter. It is evident that a portable device, such as provided by the present invention is of immediate application in all the possible emergency situations, for example outside hospital premises, at home, in ambulance or in natural catastrophe situations.

The device of the present invention is suitable for use in hemodialysis, in particular in Continuous Slow Ultrafiltration (shortly, SCUF), in Continuous Artero-Venous Hemofiltration (CAVH), or in Continuous Veno-Venous Hemofiltration (CVVH).

The device of the present invention is substantially disclosed in the main claim and in the dependent claims.

The present invention will be disclosed hereinafter according to two embodiments thereof, provided for a illustrative non-limiting purpose with reference to the annexed drawings wherein:

FIG. 1 shows a perspective view of a first embodiment of the blood filtering device according to the invention;

FIG. 2 shows an elevational section of the device of FIG. 1;

FIGS. 2A and 2B show, according to respective planes A-A and B-B in FIG. 2, two details of the device of FIG. 1;

Figure 3:
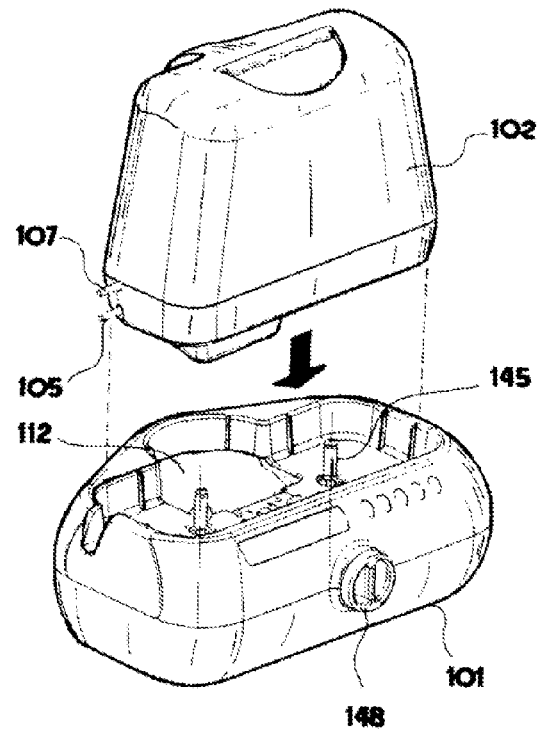
FIG. 3 shows a perspective view of a second embodiment of the blood filtering device according to the invention, in a separated configuration.

With reference to FIGS. 1, 2, 2A and 2B, a first embodiment of a blood filtering device is generally indicated as 1. It comprises a filter body 3, having an elongated shape, cylindrical in particular, with a circular section, the filter body 3, known also as hemofliter, contains membranes apt to carry out the required filtration for the treatments which will be disclosed in the following.

It comprises an inlet port integrated into the filter body, for the inlet of the blood to be filtered, to which a delivery flexible hose is connected 5 for the blood to be filtered which, as it will be appreciated in the following, is apt to be connected to further ducts, not shown, linked to a circulation, system for the taking of blood to be treated, for example to a arterovenous fistula. Essentially, the delivery hose 5 is inserted and flows into the filter body 3.

The filter body 3 further comprises an outlet port 6, to which a return hose 7 is connected for the filtered blood, and a discharge port 8, to which a discharge hose 9 is connected for the waste liquid which is accumulated inside the filter body 3.

Said inlet port is formed at one of the ends of the filter body 3, while the outlet port 6 is positioned at the opposite end.

Further, the devise comprises an independent driving body 2 housing, in a case 16, a peristaltic pump 10 divided in a peristaltic pump rotor 11 and peristaltic pump motor 12 which, in the present embodiment, is an electric stepper motor.

The rotor 11 is housed inside a peristaltic pump rotor chamber 13, which is apt to house inside a distal portion, with respect to the patient, of said flexible delivery hose 5, for obtaining a peristaltic effect. Said case 16, where it forms the rotor chamber 13, is shaped at the top in. such a way to constitute a seat or resting base 11, i.e. means for maintaining said filter body 3 in the vertical working position, wherein said inlet port, integrated into the bottom end of the filter body 3, is placed at said rotor chamber 13.

In this configuration, the case 16 operates as a basement on which the filter is positioned with a reversible joining which may be a forced or a catch joint, a screw coupling, a bayonet coupling or other equivalents.

The electric motor 12 constitutes peristaltic pump driving means 10, being connected to the rotor 11 by a drive shaft.

According to a modification, the electric motor can be separated from said rotor, the latter being engageable by crank means for the manual driving of the rotor.

It can be noted that the filter body 3, with the delivery, return, discharge flexible hoses 5, 7, 9 form a disposable kit to be associated to said case.

Through the discharge hose 9, the filter body 3 is connected to a bag or to another drainage container, for the collection of the waste liquid.

In this section, the discharge hose 9 comprises an flow adjustment system 15, for instance a Redon system. A filtering pressure adjustment system may be provided too. In the figures, a bellows pump 17 connected to the filter body is shown, utilized for triggering of the intake of the waste liquid/ which could be also drawn out by a further peristaltic pump.

It is intended that, for the employment of the device herein described, it is sufficient to use a new kit comprising filter and hoses, inserting on site the delivery hose into the peristaltic pump rotor chamber 13.

The kit will be connected to a patient circulatory system, so as to fill with blood the delivery hose 5 for triggering the peristaltic pump 10r which provides to fill the hemofliter.

According to the characteristics of the hemofilter, it is possible to carry out a patient hemodialysis without hospitalizing or moving him, in consideration of the remarkable lightness and operational easiness of the device.

At the end of the treatment, the body 2 with the peristaltic pump is ready for a new operation, while the filter and the hoses can be disposed.

Figure 4:
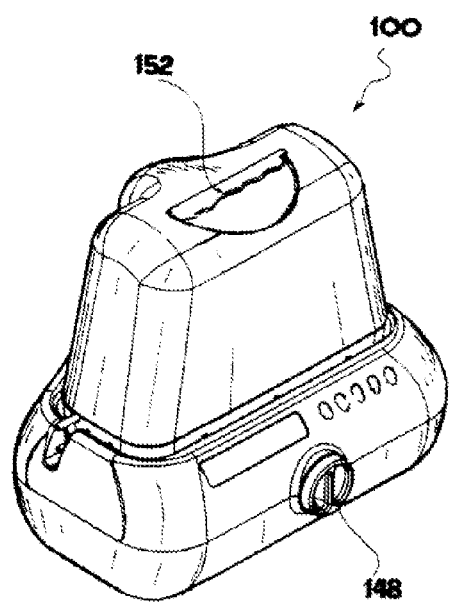
FIG. 4 shows a perspective view of the device of FIG. 3, in a joined configuration.
Figure 5:
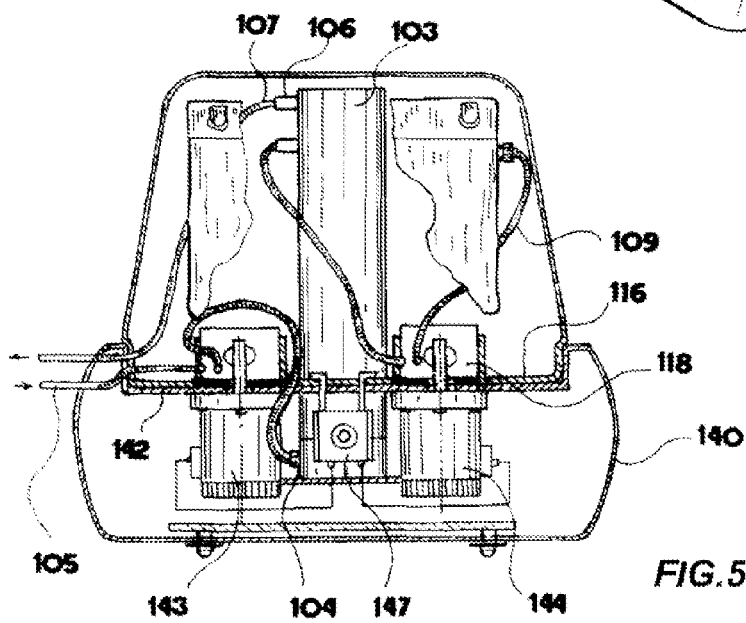
FIG. 5 shows an elevational section of the device of FIGS. 3 and 4.
Figure 5A:
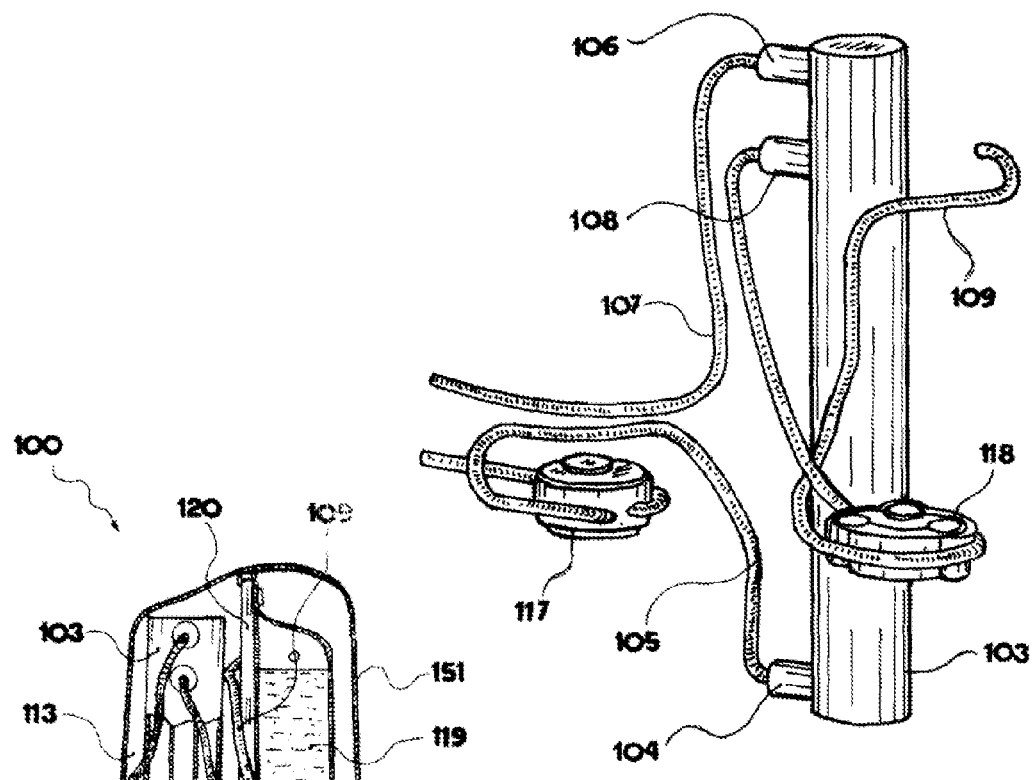
FIG. 5A shows an operational diagram of a detail of the device of FIGS. 3 and 4.
Figure 6:
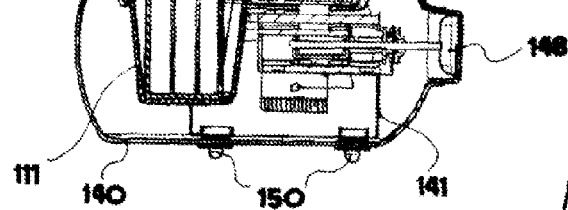
FIG. 6 shows an elevational section, according to a plane perpendicular to that of FIG. 5r of the device of FIGS. 3 and 4.
Figure 7:
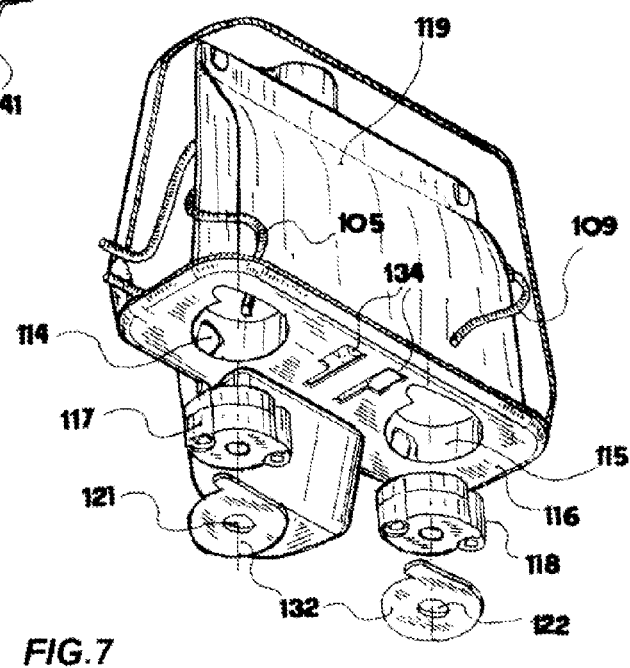
FIG. 7 shows a bottom and partially exploded perspective view of the top portion of the device of FIGS. 3 and 4.
Figures 8, 9, 10:
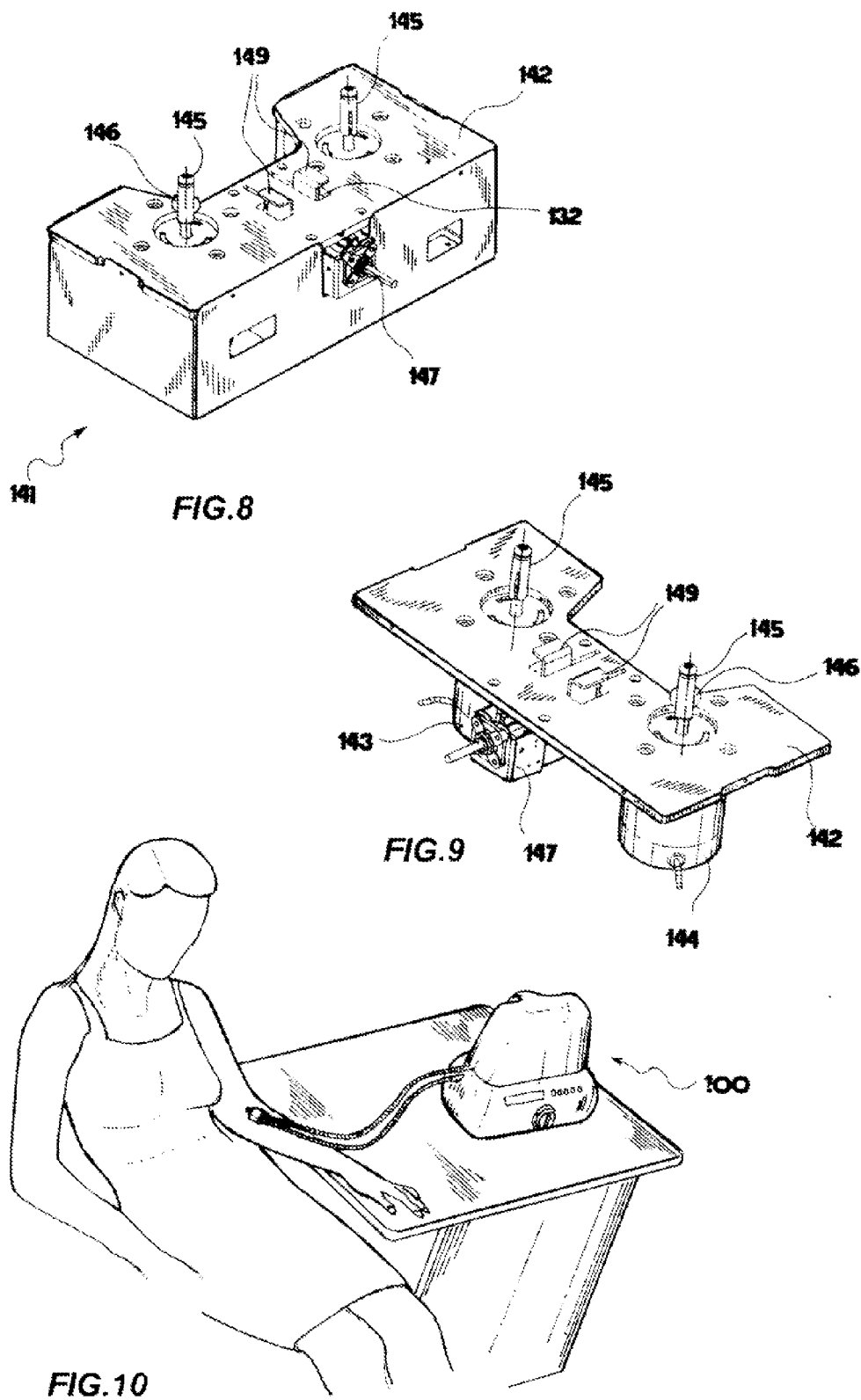
FIG. 8 shows a perspective view of the content of the bottom portion of the device of FIGS. 3 and 4.
FIG. 9 shows a perspective view of a detail shown in FIG. 8.
FIG. 10 illustrates the use of the device of FIGS. 3 and 4.

With reference to FIGS. 3 to 10, a second embodiment of the blood filtering device according to the invention is described, generally indicated by 100.

It can be divided into two detachable half-bodies, the first, indicated with 101, forming the basement of the device 100, intended to be rested on a work top.

Inside the second half-body, indicated by 102, a filter body 103 is housed, having an elongated shape and particularly cylindrical, with a circular section.

The filter body 103 contains membranes apt to carry out the required filtration in the treatments which will be described in the following.

It comprises an inlet port 104, for the inlet of the blood to be filtered, to which a delivery flexible hose 105 is connected for the blood to be filtered which, as it will be appreciated hereinafter, is apt to be connected to further ducts, not shown, and to a circulatory system for the taking of blood to be treated.

The filter body 103 further comprises an outlet port 106, to which a filtered blood return hose 107 is connected, and a discharge port 108, to which a discharge hose 109 is connected for the waste liquid lowing from the inside of the filter body 103.

Said inlet port 104 is positioned at one of the ends of the filter body 103, while the outlet port 106 is positioned at the opposite end.

The second half-body 102, completely hollow, has a bottom 110, resting on the first half-body 101, and a projection 111 projecting from said bottom 110 and inserted into a corresponding recess 112 in the first half-body 101. Said half-body 102 further has a dome covering 151, transparent, provided with an opening operating as handle 152.

Thank to the projection 111, a room 113 is formed inside the second half-body 1, having a height substantially equal to that of the whole device 100, wherein said filter body 103 is housed.

In such a way, the working position of the filter body 104 is vertical, with said inlet port 104 placed at the lower end of the filter 103.

At the bottom 110 of the second half-body 102, the device 100 comprises a pair of peristaltic pump rotor chambers, symmetrically placed with respect to the centre plane, so as to have the filter body substantially placed between them, but on a rear plane.

Said chambers, respectively indicated by 114 and 115, are formed by a case which, in the present embodiment, is made of plastic by injection moulding and forms a single piece defining said bottom 110.

Each chamber 114, 115 has entry and exit holes of a respective flexible hose and houses a peristaltic pump rotor, respectively indicated by 117, 118. This rotor 117, 118 is of the roller-type having two lobes, conveniently mounted on low friction bearings. The chambers 114, 115 are closed by a suitable lid 132 which is part of the case 116.

At the rotors 117, 118, e therefore at the lids 132, the case 116 comprises respective engagement holes 121, 122 for the introduction of a respective driving shaft, which will be discussed hereinafter, driving the rotors 117, 118.

Inside a first peristaltic pump rotor chamber 114 a portion of said delivery flexible hose 105 is positioned, for supplying the filter body 103 with blood to be filtered. Accordingly, inside a second peristaltic pump rotor chamber 115 a portion of the discharge flexible hose 109 is positioned, for the suction of the waste liquid from the filter body 103.

It should be noted how said case 116, extending from the bottom 110 with said projection 111, forms a resting base for the lower end of said filter body 103, and the inlet port 104 is placed in proximity of the corresponding first peristaltic pump rotor chamber 114. Thus, the case 116 defines means for maintaining the filter body 103 in a working position and the room 113, housing said filter body 103, is adjacent to the first rotor chamber 114, so as to minimize the length of the delivery flexible hose 105.

The case 116, i.e. the bottom of the second half-body 102, is extended so as to define a closed space comprising said room 113 and housing a collecting bag 119, for the drainage of the waste liquid drawn out of the filter body 103.

To this purpose, a mounting hanger 120 is housed inside the second half-body 102, to which the bag is hung. The bag can substantially be of a conventional type.

The first half-body 101 comprises an external case 140 and a boxed basement 141, made of metallic material, having a upper sheet 142 to which respective first and second electric motors 143, 144 are connected for driving the rotors 117, 118. They constitute driving means of said rotors.

From the motors 143, 144 respective driving shaft 145 vertically project, apt to engage the rotors 117, 118 through the holes 121, 122. Each shaft is provided with retractable fins allowing a safe securing with the corresponding rotor hole, regardless the angular position thereof.

Between the motors, electrically supplied according to conventional systems, a control system 147 is placed with a triggering and control knob 148, frontally placed on the first half-body 101.

From there, a pair of projecting elements 149 project to the upper inside a boxed container, of a catch joint system, apt to be engaged, through said upper sheet 142, into corresponding notches 134 formed in the bottom 110 of the second half-body 102.

Further, the control system 147 produces a signal of safe engagement between the two half-bodies 101, 102, i.e. allowing the operation of the peristaltic pumps.

The electric motors 143, 144 are of the stepper type.

The motors 143, 144, with their respective shaft 145, the rotors 117, 118 inserted in their respective rotor chambers 114, 115, and the corresponding flexible hose 105, 109 form peristaltic pump means for the circulation of the blood to be treated and of the waste liquid.

In the present embodiment, the shaft 143, 144 with their respective shaft 145 in turn forms means for driving the above mentioned rotors, and such means are housed in the boxed basement 141 of the device 1. The basement is apt to be placed on any plane.

This basement 141 comprises means for measuring the weight of the case, i.e. the weight of the liquid contained therein. They operate through stems 150 on which the basement 141 is mounted.

When required, it is therefore possible to easily couple the first half-body 101 placing above it the second half-body 102, so as to insert the projection 111 in the respective cavity 112, obliged engagement in consideration of the structure asymmetry.

Now, having triggered the circuit by connecting it to the artero-venous system of a patient, it is possible to drive both the peristaltic pumps, so as to start the blood filtering.

According to this embodiment of the device, it is possible to control the basic operation data, namely, the amount of extracted discharge liquid, filtration speed, etc.

In another aspect, the present invention relates to methods for treating a patient in need of ultrafiltration hemodialysis with the above disclosed device.

The method comprises connecting the patient to said device, passing blood of said patient through said device until treatment of blood according to the determination of the person skilled in the art.

In a first embodiment of the method of the present invention, said patient in need of ultrafiltration hemodialysis is a hyperhydrated patient.

The method according to the present invention is also suitable for the treatment of isolated ultrafiltration, the method is carried out as above described. Isolated ultrafiltration can be carried out in an intensive case environment, for example for resuscitation purpose or to carry out a cardiologic treatment.

In a preferred embodiment, the method according to the present invention is suitable for the treatment o a patient affected by congestive heart failure.

In general, the method according to the present invention allows to perform ultrafiltration hemodialysis in a patient outside hospital premises, by using the device disclosed herein. In a preferred embodiment, ultrafiltration hemodialysis is carried out at patient's home, conveniently, the patient lies in bed or is in a convenient position, for example in an armchair.

Under urgency conditions, the method according to the present invention is easily carried out in an ambulance. In another embodiment, the method can be carried out also in extremely critical conditions, for example in natural disaster of war fields.

Continuous Artero-Venous Hemofiltration (CAVH), or Continuous Veno-Venous Hemofiltration (CVVH) are another preferred embodiment of the method disclosed herein.

Execution of all these methods is absolutely conventional, and within the skill of the ordinary practitioner in this art, who only need of his or her basic knowledge. Usual medical handbooks are a possible source of information, for example Merck Manual of Diagnosis and Therapy.

The person skilled in this art can carry out a number of further modifications and variants to the blood filtering devices and hemodialysis methods above described in order to satisfy additional and temporary needs, which, however, are all comprised within the scope of protection of the present invention, as defined in the appended claims.

The invention claimed is:

1. Blood isolated ultrafiltration device, comprising:
   a filter body, having an inlet port and an outlet port for blood to be filtered and a discharge port for extracted waste liquid;
   a case maintaining said filter body in a working position and forming, in different portions thereof, two peristaltic pump rotor chamber, housing a corresponding peristaltic pump rotors;
   a pair of electric motors, each placed outside said case and axially to the peristaltic pump rotors, with a respective drive shaft apt to be engaged into each corresponding peristaltic pump rotor through said case;
   a delivery flexible hose of the blood to be filtered, connected to said inlet port and to further ducts linked to a circulatory system, including a portion thereof arranged inside a first peristaltic pump rotor chamber for obtaining a peristaltic effect for the circulation of blood to be filtered;
   a discharge hose of the waste liquid from the filter body, connected to said discharge port, including a portion thereof arranged inside a first peristaltic pump rotor chamber for obtaining a peristaltic effect for the waste liquid circulation,
   wherein:
      said case, with said rotor chambers and the peristaltic pump rotors, forming a disposable kit to be associated to said motors by engaging and disengaging said peristaltic pump rotors to and from said drive shafts.
      said filter body has an elongated shape, with said inlet port placed at one of the ends thereof, said working position determining said end be placed in proximity of said rotor chamber; in said working position, said filter body being vertically placed, said case forming a resting basement for the end of said filter body;

said electric motors are housed in a body case independent upon said case containing said filter body; and the basement comprises means for measuring the weight of the case, the basement being mounted on stems through which said means for measuring the weight operate.

2. Device according to claim 1, wherein said body case forms a basement on which the case containing the filter body and the peristaltic pump rotors is placed by a reversible coupling provided by said drive shafts.

3. Device according to claim 1, wherein said case houses a waste liquid collecting bag.

4. Device according to claim 3, comprising a blood return hose connected to the outlet port of the filter body, the waste liquid discharge hose being further connected to said the waste liquid collecting bag.

5. Device according to claim 1, wherein said basement is apt to be rested on any plane.

6. Device according to claim 1, wherein said drive shafts forms a catch joint system, providing the allowance to the triggering of the electric motors.

7. Device according to claim 1, wherein the electric motor is of the stepper type.

8. Device according to claim 1, wherein the peristaltic pump rotor is of two-lobes type.

9. Device according to claim 8, wherein the peristaltic pump rotor is of roller type.

10. Method for treating a patient in need of hemodialysis, comprising connecting said patient to the device of claim 1 and passing blood of said patient through said device.

11. Method for subjecting a patient to isolated ultrafiltration, comprising connecting said patient to the device of claim 1 and passing blood of said patient through said device.

12. Method according to claim 11, wherein said isolated ultrafiltration is carried out in an intensive care environment.

13. Method according to claim 12, wherein said intensive care has resuscitation purpose.

14. Method according to claim 13, wherein said intensive care has cardiologic treatment purpose.

15. Method for treating a hyperhydrated patient, comprising connecting said patient to the device of claim 1 and passing blood of said patient through said device.

16. Method for treating a patient affected by congestive heart failure, comprising connecting said patient to the device of claim 1 and passing blood of said patient through said device.

17. Method for carrying out ultrafiltration hemodialysis in a patient outside hospital premises, comprising connecting said patient to the device of claim 1 and passing blood of said patient through said device.

18. Method according to claim 17, wherein said hemodialysis is carried out at patient's home.

19. Method according to claim 17, wherein said hemodialysis is carried out in ambulance.

20. Method according to claim 17, wherein said hemodialysis is carried out in natural disaster situation.

21. Method for carrying out continuous artero-venous hemofiltration in a patient in need thereof, comprising connecting said patient to the device of claim 1 and passing blood of said patient through said device.

22. Method for carrying out continuous veno-venous hemofiltration in a patient in need thereof, comprising connecting said patient to the device of claim 1 and passing blood of said patient through said device.

* * * * *